United States Patent
Yang et al.

(10) Patent No.: US 11,406,691 B2
(45) Date of Patent: Aug. 9, 2022

(54) AMH-INH-GNIH TRI-EXPRESSION GENE VACCINE OF IMPROVING FECUNDITY OF ANIMALS, PREPARATION METHOD AND APPLICATION

(71) Applicant: Huazhong Agricultural University, Wuhan (CN)

(72) Inventors: Liguo Yang, Wuhan (CN); Jiaomei Tang, Wuhan (CN); Qunli Zhou, Wuhan (CN); Aixin Liang, Wuhan (CN); Aizhen Guo, Wuhan (CN)

(73) Assignee: Huazhong Agricultural University, Wuhan (CN)

( * ) Notice: Subject to any disclaimer, the term of this patent is extended or adjusted under 35 U.S.C. 154(b) by 8 days.

(21) Appl. No.: 17/025,486

(22) Filed: Sep. 18, 2020

(65) Prior Publication Data

US 2021/0085766 A1 Mar. 25, 2021

(30) Foreign Application Priority Data

Sep. 20, 2019 (CN) .......................... 201910892644.9

(51) Int. Cl.
*C07K 14/575* (2006.01)
*A61K 39/00* (2006.01)

(52) U.S. Cl.
CPC ........ *A61K 39/0005* (2013.01); *C07K 14/575* (2013.01); *A61K 2039/53* (2013.01); *A61K 2039/552* (2013.01); *A61K 2039/70* (2013.01); *C07K 2319/00* (2013.01)

(58) Field of Classification Search
CPC ............ A61K 2039/53; A61K 2039/70; C07K 14/575; C07K 2319/00; C07K 1/757
See application file for complete search history.

(56) References Cited

U.S. PATENT DOCUMENTS

| | | | |
|---|---|---|---|
| 6,335,170 B1 * | 1/2002 | Orntoft | C12Q 1/6886 536/24.31 |
| 6,936,417 B2 * | 8/2005 | Orntoft | C12Q 1/6886 536/23.5 |
| 11,191,749 B2 * | 12/2021 | Hum | A61K 31/426 |

* cited by examiner

*Primary Examiner* — Bao Q Li
(74) *Attorney, Agent, or Firm* — Scully, Scott, Murphy & Presser, P.C.

(57) ABSTRACT

The invention provides an AMH-INH-GNIH tri-expression gene vaccine capable of improving fecundity of animals and a preparation method of engineering strain thereof. The engineering strain was deposited in China Center for Type Culture Collection on Aug. 15, 2018, with deposit No.: CCTCC NO:M 2018544. When the engineering strain is used for direct immunization of animals or immunization of animals after being mixed with DNA vaccine adjuvant, the fecundity of the animals can be effectively improved. The tri-expression gene is a tri-expression non-resistant DNA plasmid of Mullerian duct resisting hormone, inhibin and gonadotropin release restraining hormone, which can be used for direct immunization of the animals through mucosa immunization to generate antibodies in the manner of being sprayed to noses, orally administered, blended into feeds and the like. Since the gene vaccine does not contain a resistant gene, exogenous antibiotics do not need to be introduced for screening, and antibiotic residues are not generated. Compared with other gene vaccines which need plasmid extraction and purification, high production cost and inconvenient intramuscular injection, and enable the animals to generate stress response, the gene vaccine of the invention is lower in production cost and more convenient to use, and is free from resistance and injection stress response.

8 Claims, 4 Drawing Sheets

Specification includes a Sequence Listing.

AMH-INH-GNIH TRI-EXPRESSION GENE VACCINE OF IMPROVING FECUNDITY OF ANIMALS, PREPARATION METHOD AND APPLICATION

TECHNICAL FIELD

The invention belongs to the field of biotechnology, and specifically relates to an AMH-INH-GNIH tri-expression gene vaccine for improving fecundity of animals, preparation method and application.

BACKGROUND ART

Follicle development is a cyclical process, which is comprehensively regulated by a variety of hormones, including hormones that promote follicle development, such as gonadotropin and gonadotropin releasing hormone, and hormones that inhibit follicular development, such as anti-Müllerian hormone (AMH), follicle inhibin (INH) and gonadotropin release inhibiting hormone (GnIH), etc.

AMH is a member of the transforming growth factor-$\beta$ (TGF-$\beta$) superfamily of glycoprotein involved in the regulation of growth and differentiation, and has an inhibitory effect on follicular development. Knockout of AMH can relieve its recruitment of primordial follicles and increase the number of antral follicles. AMH can weaken the stimulation of growth factor Kit ligand (KL), basic fibroblast growth factor (bFGF) and keratinocyte growth factor (KGF) on the development of primordial follicles, suggesting that AMH can reduce the transformation of primordial follicles to primary follicles, inhibit the basic and stimulative development of primordial follicles Immunohistochemical analysis of goat ovary reveals that AMH is localized in oocytes and granulosa cells (primordial follicle to antral follicle stage). Compared with the negative control, the percentage of primordial follicles of the positive control (cultured in the medium or medium with Kit ligand) decreases, the percentage of growing follicles increases, and the primordial follicles are activated. However, the addition of AMH to the culture medium shows a percentage of primordial and growing follicles similar to the negative control. These results indicate that AMH hinders the initiation of primordial follicles.

INH, which is secreted by the gonads and is a member of the transforming growth factor-$\beta$ (TGF-$\beta$) family, is a heterodimeric glycoprotein with a molecular weight of 31~34 kd. It constitute a heterodimeric glycoprotein hormone through one of the two $\beta$ subunits ($\beta$A and $\beta$B, approximately 14 kd) closely related to a subunit (18 kd). Subunit $\alpha$ and $\beta$A or $\beta$B subunits are connected by disulfide bonds to form inhibin A and inhibin B, respectively. INH is one of the important hormones in the hypothalamic-pituitary-gonadal axis regulation system. It regulates the synthesis and secretion of FSH in the body through negative feedback, and then regulates follicular development. Studies have shown that passive or active immunization with INH can promote follicular development and ovulation, increase litter size, and even improve embryo quality, thereby improving fecundity of animals. Animals immunized with INH can promote follicular development, which has a dose-dependent relationship. Han et al. (2008) used 10, 50, and 100 µg pCIS plasmids to immunize rats three times at 20-day intervals, and used 50 µg pcDNA3.1 and 100 µl 0.85% saline as controls, and found that after the second and third immunization, the average number of mature follicles in the test group was 3.6 and 4.9 more than that in the control group (P<0.05), and the average number of litters and placenta are also increased significantly. In particular, the number of mature follicles in the high-dose group (100 µg PCIS) was significantly higher than that of other test groups, which could significantly increase the number of mature follicles, but had no effect on the size and weight of the ovaries. Wang et al. (2012) immunized mice with 10, 50, 100 µg/100 µl pcISI plasmid, and used 100 µg pcMV-s and 100 µl saline as control groups, and found that the plasma FSH and estradiol concentrations of the immunized mice were both higher than the control groups (P<0.05), especially in the high-dose group (P<0.05). Compared with the control groups, the weight (P<0.05), length and width (P>0.05) of the ovaries of all immunized groups changed, especially the number of mature follicles in the high-dose group was higher than that of the other groups (P<0.05) and the number of litters increased. Mao et al. (2016) divided 120 chickens into 4 groups and injected the hens with 0, 25, 75, or 125 µg pcISI intramuscularly, and boosted them after 20 days. The results showed that the numbers of dominant follicles and large white follicles in each immunized group were higher than those in the control group (P<0.05). Especially in the high-dose group, the number of small yolk follicles increased (P<0.05), and egg production performance was significantly improved.

GnIH is a RF (arginine-phenylalanine) amide peptide (RFRP) firstly and successfully isolated and purified from quail brains by Japanese scholars in 2000. Its biological function is opposite to GnRH, mainly inhibiting the secretion of FSH (Follicle Stimulating Hormone) and LH (Luteinizing Hormone) from the anterior pituitary. Subsequently, the GnIH orthologs identified from mammalian brains were named RFamide (RFRP) related peptides, including: RFRP-1, RFRP-2, and RFRP-3. Among them, RFRP-3 is the main regulator of reproduction, with physiological function similar to inhibin in vivo. GnIH and its analogs can not only act on the hypothalamus pituitary and GnRH neuron through GPR147, but also inhibit the synthesis and release of gonadotropins and the development and maintenance of gonads. In the different development stages of mammalian reproduction, including pre-estrus, puberty, estrus cycle, pregnancy, lactation, menopause and ovarian diseases, RFRPs have been proven to be key mediators of ovarian development and potential inhibitory regulators of GnRH release, which may indirectly exert its influence on follicular development through the upstream regulators of GnRH, or directly exert its influence through a subset of GnRH neurons. In addition to regulating the secretion of gonadotropins, GnIH further regulates reproductive behavior by changing the biosynthesis of neurosteroids in the brain. GnIH can inhibit the release of LH and FSH from the pituitary gland of chicken and quail. Intravenous administration of RFRP-3 can reduce the level of gonadotropin in the peripheral blood of gonadalectomy male rats, inhibit the production of testosterone steroid hormones and spermatogenesis in adult mice, the pulse amplitude of sheep LH, and inhibit the secretion of LH and FSH. Moreover, studies have shown that GnIH inhibits follicular development and steroid production in chickens. The above studies suggest that GnIH may directly or indirectly inhibit follicular development and ovulation.

SUMMARY OF THE INVENTION

The object of the present invention is to provide an engineering strain of AMH-INH-GNIH tri-expression gene vaccine capable of improving the fecundity of animals. Another object of the present invention is to provide a co-expression plasmid of non-resistant screened anti-müllerian hormone, inhibin and gonadotropin release-inhibiting hormone; this plasmid can be used as a DNA vaccine to immunize animals for improving the fecundity of animals and overcoming some technical difficulties.

In order to achieve the above objects, the present invention adopts the following technical solutions:

An engineering strain of the AMH-INH-GNIH tri-expression gene vaccine with the function of improving the fecundity of animals. The engineering strain was deposited in China Center for Type Culture Collection on Aug. 15, 2018, with the deposit number: CCTCC NO: M 2018544.

The AMH-INH-GNIH tri-expression gene vaccine prepared from the above-mentioned engineering strain can be obtained by SDS alkaline lysis extraction to obtain the AMH-INH-GNIH tri-expression plasmid (PVAX-tPA-SAMH-2A-tPA-SINH-2A'-tPA-SRFRP-asd plasmid).

An AMH-INH-GNIH tri-expression gene vaccine capable of improving the fecundity of animals is characterized in that it includes tPA-SAMH gene, tPA-SINH gene and tPA-SRFRP gene in sequence.

For the AMH-INH-GNIH tri-expression gene vaccine as described above, the gene sequence of tPA-SINH is shown in SEQ ID NO. 1, and the gene sequence of tPA-SRFRP is shown in SEQ ID NO. 2. The gene sequence of tPA-SAMH is shown in SEQ ID NO.3.

For the AMH-INH-GNIH tri-expression gene vaccine as described above, 2A peptide is connected between the tPA-SAMH gene and the tPA-SINH gene, and 2A' peptide is connected between the tPA-SINH gene and the tPA-SRFRP gene. The gene sequence of the 2A peptide is shown in SEQ ID NO. 4; the gene sequence of the 2A' peptide is shown in SEQ ID NO. 5.

A method for preparing an AMH-INH-GNIH tri-expression gene vaccine for improving the fecundity of animals as described above, which includes the following steps:

S1. constructing PVAX-tPA-SAMH-2A-tPA-SRFRP-asd and PVAX-tPA-SINH-2A'-tPA-SRFRP-asd double expression plasmids;

S2. enzyme digesting the plasmids obtained in step 51 with Hind III and BamH I, respectively, followed by ligation to obtain a PVAX-tPA-SAMH-2A-tPA-SINH-2A'-tPA-SRFRP-asd tri-expression plasmid.

In the above method, the PVAX-tPA-SINH-2A'-tPA-SRPRP-asd plasmid was constructed using the following method:

S1101, using PVAX-tPA-SINH-asd as a template to amplify the tPA-SINH gene fragments; wherein the gene sequence of the tPA-SINH PCR is shown in SEQ ID NO.1, Using PVAX-tPA-SRFRP-asd as a template to amplify the tPA-SRFRP gene fragment; wherein the sequence of the tPA-SRFRP gene fragment is shown in SEQ ID NO.2.

S1102 enzyme digesting the PCR products of pVAX-asd and tPA-SRFRF with EcoRI and XhoI, followed by ligation to obtain a plasmid PVAX-tPA-SRFRP-asd;

S1103. Enzyme digesting the PCR products of PVAX-tPA-SRFRP-asd and tPA-SINH with BamH I and EcoRI, followed by ligation to obtain a plasmid PVAX-tPA-SINH-tPA-SRFRP-asd;

S1104. Enzyme digesting PVAX-tPA-SINH-tPA-SRFRP-asd and PUC57-2A'-2A' plasmids with EcoRI, followed by ligation to obtain a plasmid PVAX-tPA-SINH-2A'-tPA-SRFRP-asd; wherein the gene sequence of the 2A' peptide is shown in SEQ ID NO.5, In the above method, the PVAX-tPA-SAMH-2A-tPA-SRFRP-asd plasmid was constructed using the following method:

S1201. Enzyme digesting the PVAX-tPA-SRFRP-asd and tPA-SAMH PCR products with Hind III and Kpn I, followed by ligation to obtain a plasmid PVAX-tPA-SAMH-tPA-SRFRP-asd; wherein the gene sequence of the tPA-SAMH PCR product is shown in SEQ ID NO.3;

S1202, enzyme digesting PVAX-tPA-SAMH-tPA-SRFRP-asd and PUC57-2A'-2A plasmids with Kpn I and BamH I, followed by ligation to obtain a plasmid PVAX-tPA-SAMH-2A-tPA-SRFRP-asd; wherein the gene sequence of the 2A peptide is shown in SEQ ID NO.4;

S1203. Enzyme digesting the PVAX-tPA-SAMH-2A-tPA-SRFRP-asd and PVAX-tPA-SINH-2A'-tPA-SRFRP-asd plasmids with Hind III and BamH I, followed by ligation to obtain the plasmid PVAX-tPA-SAMH-2A-tPA-SINH-2A'-tPA-SRFRP-asd.

Provided is a use of the above-mentioned AMH-INH-GNIH tri-expression gene vaccine for improving the fecundity of animals or the vaccine prepared by the method described above in the preparation of medicines for improving the fecundity of animals.

The engineering strain containing the AMH-INH-GNIH tri-expression gene vaccine to improve the fertility of animals (PVAX-tPA-SAMH-2A-tPA-SINH-2A'-tPA-SRFRP-asd) directly used to immunize animals or mixed with DNA vaccine adjuvants to immunize animals can improve the fecundity of animals.

The beneficial effects of the present invention are given below:

The present invention provides a non-resistant screened co-expression plasmid of anti-müllerian hormone, inhibin and gonadotropin inhibiting hormone, which has the following advantages:

1. Tri-expression non-resistant DNA plasmid PVAX-tPA-SAMH-2A-tPA-SINH-2A'-tPA-SRFRP-asd of anti-müllerian hormone, inhibin and gonadotropin inhibiting hormone can express three proteins of anti-müllerian hormone (AMH), inhibin (INH) and gonadotropin inhibiting hormone (RFRP) with strong immunogenicity which stimulate mice to produce higher antibody levels.

2. After immunizing mice by gavage, the engineering strain C500 (PVAX-tPA-SAMH-2A-tPA-SINH-2A'-tPA-SRFRP-asd) containing AMH-INH-GNIH tri-expression gene vaccine that improves the fecundity of animals produces anti-müllerian hormone, inhibin and gonadotropin inhibiting hormone antibodies, neutralizes endogenous hormones, weakens the inhibitory effect of these three hormones on gonadotropins, and promotes the reproduction of mice, and the litter size (15.9±1.90) is significantly higher than PBS control group (13.7±1.72) and blank plasmid control group (13.7±2.30), and also higher than AMH single expression group (14.35±2.43), INH single expression group (14.94±2.19), RFRP Single expression group (14.26±1.37), double expression group (PVAX-tPA-SAMH-2A-tPA-SRFRP-asd, 15.50±3.14) and double expression group (PVAX-tPA-SINH-2A'-tPA-SRFRP-asd, 15.44±2.1), the effect of promoting reproduction is significant.

3. The engineering strain C500 (PVAX-tPA-SAMH-2A-tPA-SINH-2A'-tPA-SRFRP-asd) containing tri-expression non-resistant DNA plasmid of anti-müllerian hormone, inhibin and gonadotropin inhibiting hormone can directly immunize animals through nasal spray, oral administration, mixed feeding, and other means to produce antibodies through mucosal immunization. Because it does not contain resistance genes and no exogenous antibiotics need to be introduced for screening, no antibiotic residues are produced. Compared with other gene vaccines that need plasmid extraction and purification, highproduction cost, and troublesome intramuscular injection, and cause stress response of animals. The vaccine of the present invention has low productioncost, is convenient to use, and has no resistance and injection stress response.

Figure 2:
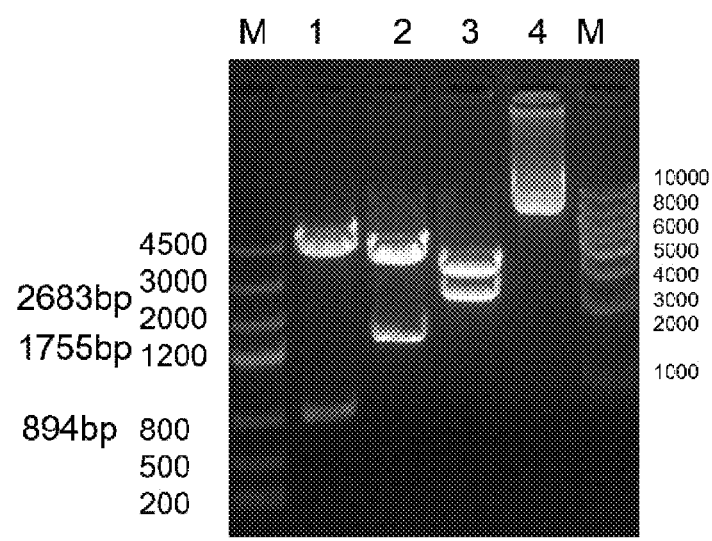

FIG. 2 shows an electrophoresis diagram of PVAX-SAMH-2A-SINH-2A'-SRFRP-asd plasmid after enzyme digestion; wherein, M: Marker III; Lane 1: HindIII/BamHI; Lane 2: HindIII/EcoRI; Lane 3: HindIII/)(ha Lane 4: plasmid; M: 1 kb DNA Ladder Marker.

Figure 3:
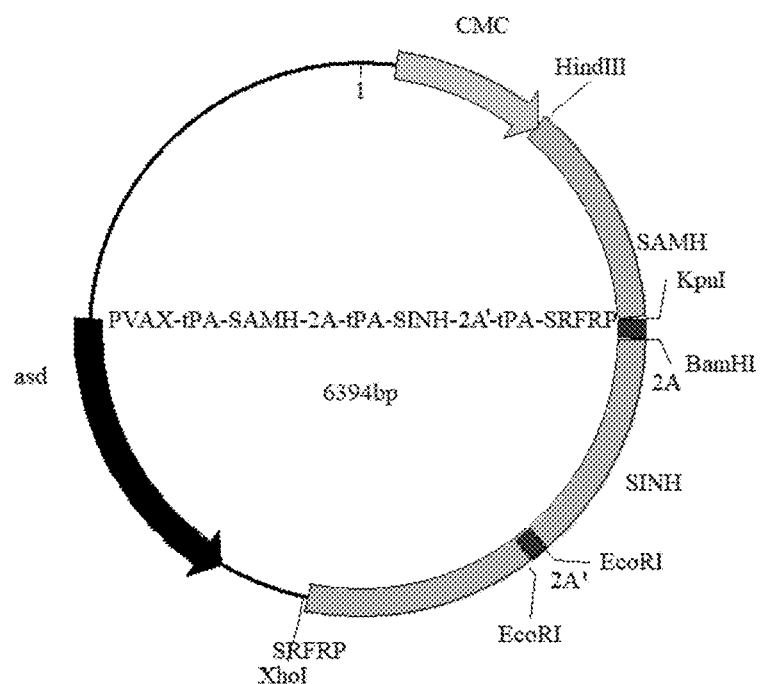

FIG. 3 shows a diagram of PVAX-SAMH-2A-SINH-2A'-SRFRP-asd plasmid.

Figure 4:
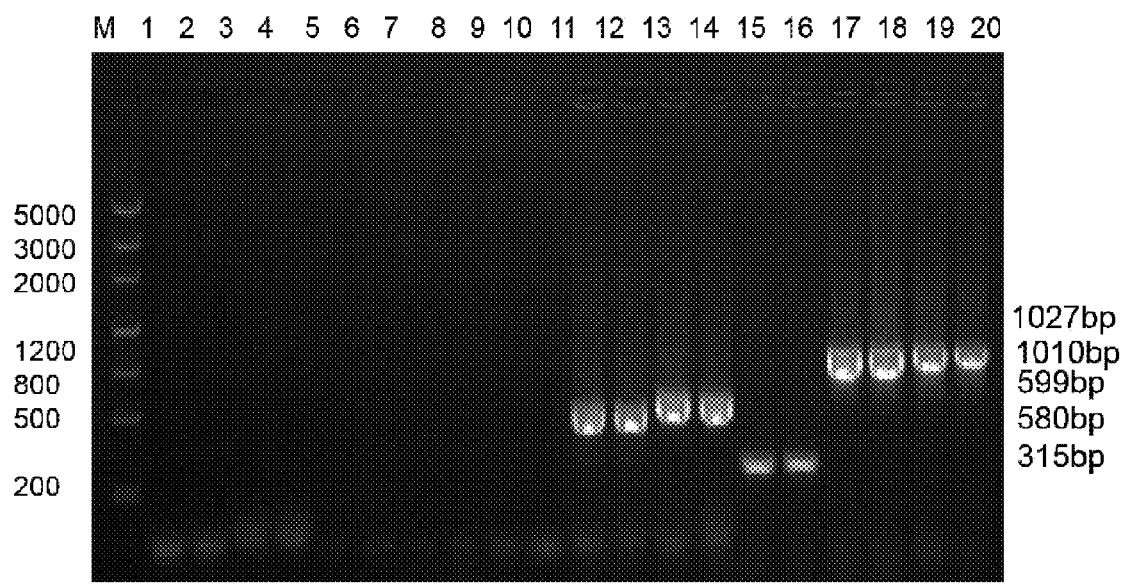

FIG. 4 shows a PCR identification of PVAX-SAMH-2A-SINH-2A'-SRFRP-asd C500, M: Marker III; Lanes 1-2: InvA negative; Lanes 3-4: Crp negative; Lanes 5-6: Asd negative; Lanes 7-8: AMH-INH negative; Lanes 9-10: INH-GnIH negative; Lanes 11-12: InvA; Lane 13-14: Crp; Lanes 15-16:Asd; Lanes 17-18: AMH-INH Fragment; Lanes 19-20: INH-GnIH fragment.

Figure 5:
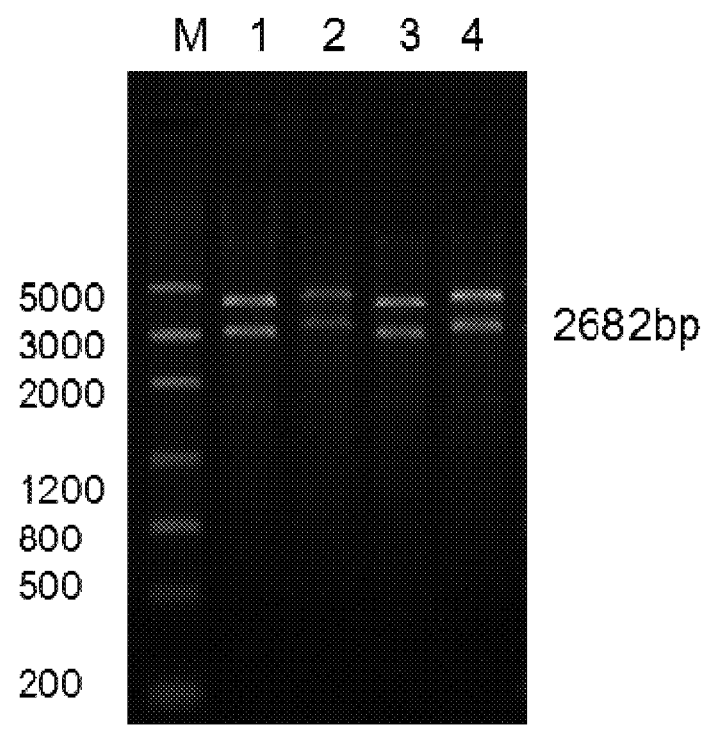

FIG. 5 shows an enzyme digestion diagram of PVAX-SAMH-2A-SINH-2A'-SRFRP-asd plasmid after purification; wherein, M: Marker III; lanes 1-4: HindIII/XhoI.

Figure 6:
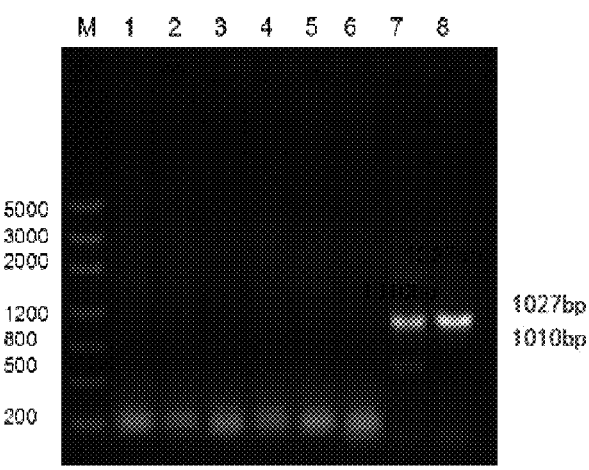

FIG. 6 shows a diagram of the transcription level of PVAX-SAMH-2A-SINH-2A'-SRFRP-asd transfected HELA cells; wherein, M: Marker III; Lane 1: AMH-INH negative; Lane 2: INH-RFRP negative; Lane 3: AMH-INH without treatment; Lane 4: INH-RFRP without treatment; Lane 5: AMH-INH transfection with empty vector; Lane 6: INH-RFRP transfection with empty vector; Lane 7: AMH-INH transfected tri-expressions; Lane 8: INH-RFRP transfected tri-expressions.

Figure 7:
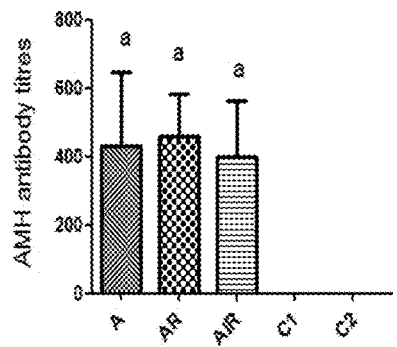

FIG. 7 shows the levels of anti-AMH antibodies in mice immunized with different vaccines.

Figure 8:
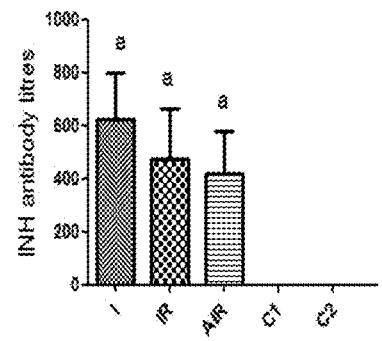

FIG. 8 shows the levels of anti-INH antibodies in mice immunized with different vaccines.

Figure 9:
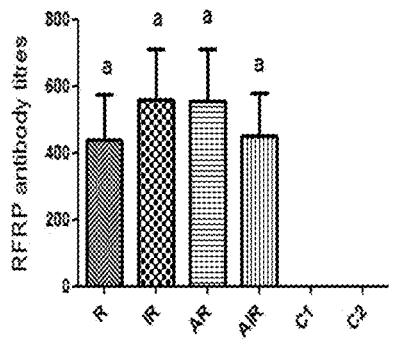

FIG. 9 shows the levels of anti-RFRP antibodies in mice immunized with different vaccines.

SPECIFIC MODE FOR CARRYING OUT EMBODIMENTS

Existing research shows that GnIH may directly or indirectly inhibit follicular development and ovulation. However, the inventors have used GnIH gene vaccine to immunize sheep and mice through a large number of experiments, and found that they can stimulate follicle development and ovulation, and increase litter size. INH is one of the important hormones in the hypothalamic-pituitary-gonadal axis regulation system. It inhibits the synthesis and secretion of FSH in the body through feedback, and has a regulatory effect on follicular development. GnIH at the most upstream level of the HPG axis reduces the circulating levels of gonadotropins (LH and FSH) and gonadal steroids by inhibiting the activity of GnRH neurons. AMH can reduce the conversion of primordial follicles to primary follicles, inhibit the basic and stimulative development of primordial follicles (Nilsson et al., 2007). The ovaries of AMH knockout female mice will show exhaustion of primordial follicles (Durlinger et al., 1999). AMH, INH and GnIH have different inhibitory mechanisms for follicular development. The former directly inhibits the development of small follicles, while the latter two inhibit the development of large follicles by inhibiting the secretion of pituitary FSH; it can be seen from the above that if the three are used in combination, they will inhibit follicular development, reduce reproductive ability, but the inventor of the present invention found that among the three hormones that inhibit follicular development, if only one or two of them are immunoneutralized, the inhibitory effect of the remaining two or one hormone will be enhanced. Therefore, neutralizing the three endogenous hormones at the same time can relieve the inhibitory effects of the above three hormones, thereby improving the effect of follicle development. It is believed that there may be a compensatory effect among INH, GnIH and AMH and it is predicted that neutralizing INH, GnIH and AMH at the same time may have a better effect on improving the fecundity of animals. When it is necessary to construct a plasmid that expresses multiple genes, bicistronic or polycistronic expression vectors can be used. In various strategies for constructing multiple expression genes, the internal ribosome entry site (IRES) is widely used. However, due to the large volume of IRES, usually more than 500 nucleotides, and the large difference in expression levels between the genes before and after (the expression amount of downstream genes is about 10%-50% of the upstream), a new strategy is needed to replace IRES. In the present invention, a large number of studies have found that the self-cleaving 2A peptide is used to replace IRES, because it is small (18-22 amino acids) and has a high enzyme digestion efficiency between the upstream and downstream genes of the 2A peptide (almost equimolar expression happens on upstream and downstream). Therefore, in order to enable the efficient expression of multiple expression genes, this study used 2A peptide as a linker, optimized the gene sequence of 2A peptide, and constructed plasmid pVAX-tPA-SAMH-2A-tPA-SINH-2A'-tPA-SRFRP-asd. After a large number of experiments, the sequence of each gene used capable of effective expression is liseted as follows: the gene sequence used for determination of tPA-SINH is shown in SEQ ID NO.1, and the gene sequence used for determination of tPA-SRFRP is shown in SEQ ID NO.2 The gene sequence used by tPA-SAMH is shown in SEQ ID NO.3; the gene sequence used by 2A peptide is shown in SEQ ID NO.4; the gene sequence used by 2A' peptide is shown in SEQ ID NO.5.

The following examples are used to further illustrate the present invention, but should not be construed as limiting the present invention. Without departing from the spirit and essence of the present invention, modifications or substitutions made to the present invention belong to the scope of the present invention.

Unless otherwise specified, the technical means used in the embodiments are conventional means well known to those skilled in the art. The reagents or raw materials, unless otherwise specified, all come from commercial channels.

Example 1 Construction of an Eukaryotic Tri-Expression Anti-müllerian Hormone, Inhibin, and Gonadotropin Inhibiting Hormone Plasmid PVAX-tPA-SAMH-2A-tPA-SINH-2A'-tPA-SRFRP-asd 1. Construction of a double expression PVAX-tPA-SINH-2A'-tPA-SRFRP-asd plasmid;

1) PVAX-tPA-SINH-asd as a template (constructed by Huazhong Agricultural University, see Appendix 1 for specific operations) was used to amplify the tPA-SINH gene fragment; wherein the primers used are shown in Table 1, the amplified tPA-SINH gene fragment was shown in SEQ ID NO.1, PVAX-tPA-SRFRP-asd as a template (constructed by Huazhong Agricultural University, see Appendix 2 for specific operations) was used to amplify the tPA-SRFRP gene fragment; the primers used were shown in Table 1, the amplified tPA-SRFRP gene fragment was shown in SEQ ID NO.2;

2) Enzyme digestion of pVAX-asd and tPA-SRFRP PCR products was conducted with EcoRI and XhoI, and plasmid PVAX-tPA-SRFRP-asd was obtained after ligation;

3) Enzyme digestion of PVAX-tPA-SRFRP-asd and tPA-SINH PCR products was conducted with BamH I and EcoRI, and plasmid PVAX-tPA-SINH-tPA-SRFRP-asd was obtained after ligation;

4) Enzyme digestion of the plasmids of PVAX-tPA-SINH-tPA-SRFRP-asd and PUC57-2A'-2A (the target fragments were linked to the PUC57 vector, synthesized by Shanghai Sangon Biotech) was conducted with EcoRI, and the plasmid PVAX-tPA-SINH-2A'-tPA-SRFRP-asd was obtained after ligation; the gene sequence of 2A' in PUC57-2A'-2A was shown in SEQ ID NO.5;

TABLE 1

The primer sequences of tPA-SINH and tPA-SRFRP

| Gene Name | Primer Sequence (5'-3') | Enzyme Digestion Site | Size | Annealing Temperature |
|---|---|---|---|---|
| tPA-SINH | SEQ ID NO.6: F: 5'-CGCGGATCCGCCACCATGGATGCAATGAAGAGAGGGC-3' | BamHI | 873 bp | 58° C. |
| | SEQ ID NO.7: R:-5'-CCGGAATTCTTEGTCTGTGGCAGTCGGCG-3' | EcoRI | | |
| tPA-SRFRP | SEQ ID NO.8: F: 5'-CCGGAATTCGCCACCATGGATGCAATGAAGAGAGGGC-3' | EcoRI | 867 bp | 58° C. |
| | SEQ ID NO.9: R: 5'-CCGCTCGAGTTAAATGTATACAAACCTCTGGGGC-3' | XhoI | | |

2. Construction of PVAX-tPA-SAMH-2A-tPA-SRFRP-asd plasmid;

PVAX-tPA-SAMH-asd as a template (constructed by Huazhong Agricultural University, see Appendix 3 for specific operations) was used to amplify the tPA-SAMH gene fragment; the primers used were shown in Table 2, and the amplified tPA-SAMH gene fragment was shown in SEQ ID NO.3, 5) Enzyme digestion of the PVAX-tPA-SRFRP-asd and tPA-SAMH PCR products was conducted with Hind III and Kpn I, and the plasmid PVAX-tPA-SAMH-tPA-SRFRP-asd was obtained after ligation;

6) Enzyme digestion of PVAX-tPA-SAMH-tPA-SRFRP-asd and PUC57-2A'-2A plasmids (the target fragment was linked to the PUC57 vector, synthesized by Shanghai Sangon Biotech) was conducted with Kpn I and BamH I, and the plasmid PVAX-tPA-SAMH-2A-tPA-SRFRP-asd was obtained after ligation; the gene sequence of 2A in PUC57-2A'-2A was shown in SEQ ID NO.4;

7) Enzyme digestion of PVAX-tPA-SAMH-2A-tPA-SRFRP-asd and PVAX-tPA-SINH-2A'-tPA-SRFRP-asd plasmids was conducted with Hind III and BamH I, and the plasmid PVAX-tPA-SAMH-2A-tPA-SINH-2A'-tPA-SRPRP-asd was obtained after ligation;

TABLE 2

The primer sequences of tPA-SAMH

| Gene Name | Primer Sequence (5'-3') | Enzyme Digestion site | Size | Annealing Temerature |
|---|---|---|---|---|
| tPA-SAMH | SEQ ID NO. 10: F:5'-CCGAAGCTTGCCACCATGGATGCAATGAAGAGAGGGC-3' | Hind III | 843 bp | 58° C. |
| | SEQ ID NO. 11: R:-5'-CCGGGTACCTTGCTGAAAGATGAGTGTCCCG-3' | Kpn I | | |

3. Enzyme digestion of PVAX-tPA-SINH-2A'-tPA-SRFRP-asd and PVAX-tPA-SAM H-2A-tPA-SRFRP-asd plasmids was conducted with Hind III and BamH I, respectively, and Enzyme digestion of PVAX-tPA-SAMH-2A-TPA-SR-FRP-asd plasmid was conducted to obtain the fragment tPA-SAMH-2A (894 bp), (PVAX-tPA-SINH-2A'-tPA-SR-FRP-asd was 5512 bp, PVAX-tPA-SAMH-2A-tPA-SRFRP-asd was 4581 bp), in which the total volume of the reaction system was 20 µl, which contained:

| | |
|---|---|
| DNA plasmid | ≤1 µg |
| 10 × FastDigest Buffer | 2 µl |

-continued

Figure 1:
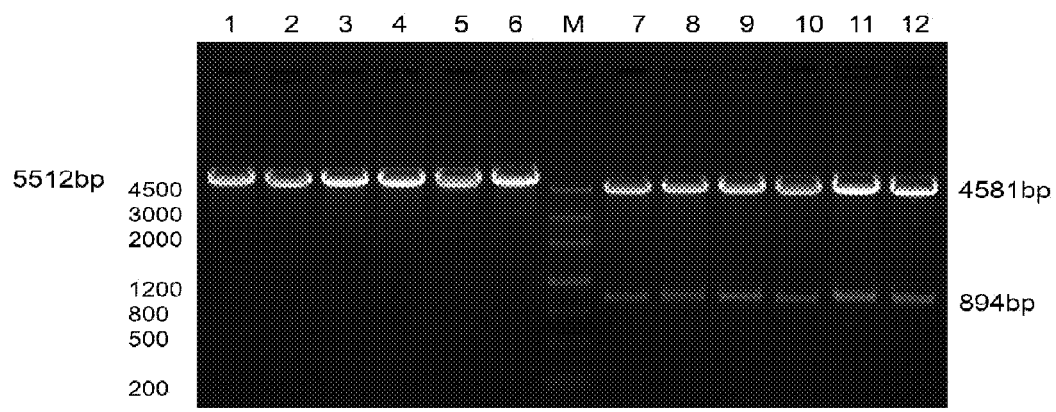
FIG. 1 shows an enzyme digestion diagram of PVAX-tPA-SINH-2A'-tPA-SRFRP-asd and PVAX-tPA-SAMH-2A-tPA-SRFRP-asd plasmids; wherein, M: Marker III; Lanes 1-6: the enzyme digested product of PVAX-tPA-SINH-2A'- tPA-SRPRP-asd plasmid; Lanes 7-12: the enzyme digested product of PVAX-tPA-SAMH-2A-tPA-SRFRP-asd plasmid.

| | |
|---|---|
| Hind III | 1 µl |
| BamH I | 1 µl |
| ddH$_2$O | to 20 µl | the reaction was conducted in 37° C. water bath for 1h;

finally, the enzyme digested products were electrophoresed on a 1% agarose gel with Marker III as the molecular weight standard, and the results of electrophoresis were observed and shown in FIG. 1, wherein M: Marker III; lanes 1-6: enzyme digested products of PVAX-tPA-SINH-2A'-tPA-SRFRP-asd plasmid; lanes 7-12: enzyme digested products of PVAX-tPA-SAMH-2A-tPA-SRFRP-asd plasmid.

3) Ligation: the gel recovery kit was used to recover the enzyme digested products (see the OMEGA Gel Extraction Kit instruction manual). After the products were recovered, Takara ligase was used to ligate the target fragment and the vector. The total volume of the ligation system was 10 µl:

| | |
|---|---|
| 10 × ligation Buffer | 1 µl |
| T4 DNA ligation | 1 µl |
| PVAX-tPA-SINH-2A'-tPA-SRFRP-asd | 2 µl |
| SAMH-2A fragment | 6 µl |

After overnight at 16° C., the ligation product PVAX-tPA-SAMH-2A-tPA-SRFRP-asd can be used directly for transformation or stored at −20° C. for later use.

3) Recombinant plasmid PVAX-tPA-SAMH-2A-tPA-SR-FRP-asd was transformed into competent bacteria: the ligation product was transformed into competent bacteria χ6097 by heat shock method, the method was given below:

(1) 10 µl of recombinant DNA (PVAX-tPA-SAMH-2A-tPA-SINH-2A'-tPA-SRFRP-asd) was added to 100 µl of the competent cells melted in an ice bath, mixed gently, and placed in an ice bath for 30 minutes.

(2) the tube was heated in a 42° C. water bath for 90 seconds, then quickly transferred to the tube to an ice bath for 2 minutes. Do not shake the centrifuge tube during this process.

(3) 900 µl of sterile LB medium (without antibiotics) was added to each centrifuge tube, mixed well and placed at 37° C. and incubated at 220 r/min for 45 minutes to resuscitate the bacteria.

(4) the tube was centrifuged at 1000 rpm for 5 min, the supernatant was aspirated and discarded, and an appropriate amount of the supernatant was left.

(5) the precipitate was gently blowed up, mixed well, and transferred to LB solid medium (without antibiotics), and the cells were evenly spread. the plate was placed in a 37° C. incubator, inverted after 30 minutes, and incubated at 37° C. overnight.

4) Screening, identification and sequencing of PVAX-tPA-SAMH-2A-tPA-SINH-2A'-tPA-SRFRP-asd positive clones: the positive clones were picked from the plates in the previous step (PVAX-tPA-SAMH-2A-tPA-SINH-2A'-tPA-SRFRP-asd), and inoculated in LB liquid culture medium, and the plasmid was extracted with plasmid mini kit, enzyme digested with restriction enzymes HindIII/BamHI, HindIII/EcoRI and HindIII/XhoI, and reacted at 37° C. for 1 h, and the results of enzyme digestion was observed by 1.0% agarose gel electrophoresis. The results were shown in FIG. 2, wherein M: Marker III; Lane 1: HindIII/BamHI double enzyme digestion; Lane 2: HindIII/EcoRI double enzyme digestion; Lane 3: HindIII/XhoI double enzyme digestion; Lane 4: Plasmid; M:1 kb DNA Ladder Marker, indicating the electrophoresis band and the target band (wherein 894 bp was tPA-SAMH-2A, 1755 bp was tPA-SAMH-2A-tPA-SINH, 2683 bp was tPA-SAMH-2A-tPA-SINH-2A'-tPA-SRPRP) matched in size, the sequencing results are correct, and the eukaryotic expression plasmid vector PVAX-tPA-SAMH-2A-tPA-SINH-2A'-tPA-SRFRP-asd was obtained (shown in FIG. 3).

Example 2: Preparation of Eukaryotic Tri-Expression Anti-müllerian Hormone Inhibin Gonadotropin Release-Inhibiting Hormone Plasmid PVAX-tPA-SAMH-2A-tPA-SINH-2A'-tPA-SRFRP-asd C500 Competent Engineering Strain

1. Preparation of Competent Cells

A sterile inoculating loop was used to pick the cryopreserved *Salmonella cholerae* suis C500 to streak on the LB agar plate containing DAP (50 µg/ml), and streak on the LB agar plate without DAP as a control, and cultured overnight at 37° C. The next day, a single colony that grew well was picked and placed in 5 ml LB liquid medium containing DAP (50 µg/ml), and cultured overnight at 37° C. under shaking. 3 ml of the activated culture was inoculated into 300 ml of LB liquid medium containing DAP (50 µg/ml), and cultured under shaking at 37° C. for 2.5-3 hours to achieve an OD600 value of about 0.5. The strain culture was poured into a pre-cooled sterile centrifuge bottle under aseptic conditions, placed in an ice bath for 30 minutes and centrifuged at 4° C. at 5000 rpm/min for 10 minutes, and the supernatant was completely discarded, and the strain precipitants were gently suspended with 10 ml of ice-pre-cooled 10% glycerol solution, placed in an ice bath for 10 min, and centrifuged at 4° C. at 5000 rpm/min for 10 min, and the supernatant was discarded. Repeatedly, the strain precipitants were gently suspended with 10 ml of ice-pre-cooled 10% glycerol solution, placed in an ice bath for 10 min, and centrifuged for 10 min, the supernatant was discarded, and finally the strain precipitants were resuspended with 10 ml of ice-pre-cooled 10% glycerol, and the suspended competent cells were divided into 80 µl and used immediately for electrotransformation or stored in a −80° C. refrigerator for later use.

2. Electrotransformation of C500 with Plasmid

20 µl of the plasmid was added to fresh 80 µl of competent cells, mixed and pre-cooled on ice for 30 min. The electroporator parameters were set as follows: voltage 1.8 KV, time 4 ms-6 ms. The cooled mixture was added to the electric cup, the electric shock was given after the water was wiped off outside of the cup, the SOC medium was immediately added and resuscitates at 37° C. on a shaking table for 45 minutes. After centrifuge at 8000 rpm/min for 1 min, the supernatant was aspirated and discarded, and the rest was spread on a MacConkey solid plate preheated in an incubator, and incubated overnight at 37° C.

3. PCR Identification

A single colony from the MacConkey plate was added in LB medium without any antibiotics, and PCR method was used to identify and screen positive clones, mainly for detection of Crp, Asd, InvA, INH-RFRP, AMH-INH genes, InvA, Crp and Asd were detected whether they were the target strains; AMH-INH and INH-RFRP were detected whether the target strains had been transfected with the target plasmid. The 20 µl PCR reaction system used contained upstream and downstream primers 1 µl/each (see Table 3 for primer sequences), 2×Taq PCR Mix 10 µl, template 2 µl, and ddH2O 6 µl. The reaction program was: pre-denaturating at 94° C. for 4 min, then denaturating at 94° C. for 40 sec, annealing at 58° C. for 30 sec, extending at 72° C. for 50 sec, totalling 35 cycles, and finally extending at 72° C. for 10 min. The results were shown in FIG. 4, wherein M: Marker III; Lanes 1-2: InvA negative control; Lanes 3-4: Crp negative control; Lanes 5-6: Asd negative control; Lanes 7-8: Primer AMH-INH negative control; Lanes 9-10: Primer INH-RFRP negative control; Lanes 11-12: InvA amplification of strain solution; Lanes 13-14: Crp amplification of strain liquid; Lanes 15-16: Asd amplification of strain liquied; Lanes 17-18: AMH-INH fragment amplification of strain liquid; Lanes 19-20: INH-RFRP fragment amplification of strain liquid.

TABLE 3

Primer characteristics of genes cloned

| Gene Name | Primer Sequence (5'-3') | Size |
|---|---|---|
| Crp | SEQ ID NO. 12: F:5'-TACG CGCATACAACAAAAGTCGC-3' | 599 bp |
| | SEQ ID NO. 13: R:-5'-GCC ATTCTGACGGAATTAACGGG-3' | |
| Asd | SEQ ID NO. 14: F:5'-TTGC TTTCCAACTGCTGAGC-3' | 315 bp |
| | SEQ ID NO. 15: R:-5'-TCC TATCTGCGTCGTCCTAC-3' | |
| InvA | SEQ ID NO. 16: F:5'-CAGG ATACCTATAGTGCTGC-3' | 580 bp |

TABLE 3-continued

Primer characteristics of genes cloned

| Gene Name | Primer Sequence (5'-3') | Size |
|---|---|---|
| | SEQ ID NO. 17: R:-5'-CGC ACCGTCAAAGGAACCGT-3' | |
| INH-RFRP | SEQ ID NO. 18: F:5'-TATG TCCACCGCCCCTCTG-3' | 1027 bp |
| | SEQ ID NO. 19: R:5'-AATG TATACAAACCTCTGGGCA-3' | |
| AMH-INH | SEQ ID NO. 20: F:5'-ATGA GGGAAGAGGTCTCCAATA-3 | 1010 bp |
| | SEQ ID NO. 21: R:-5'-TCT TGTCTGTGGCAGTCGGC-3' | |

4. Plasmid extraction by alkaline lysis method (1) a single colony from the MacConkey plate was placed in 5 ml of LB medium without any antibiotics, and cultured overnight at 37° C. under shaking at 220 rpm/min.

(2) 2 ml of strain solution was transferred into a 2 ml of EP tube, centrifuged at 13000 rpm for 1 min, and the supernatant was discarded.

(3) the precipitate was suspended in 100 μl of ice-cold Solution I, vortexed and shaken until the strains were fully suspended.

(4) 200 μl of newly prepared Solution II was added, immediately inverted and mixed well, and placed in ice bath for 5 minutes. 150 μl of ice-cold Solution III was added, gently mixed upside down, and then placed in ice bath for 5 minutes.

(5) the mixture was centrifuged at 13000 rpm for 5 minutes, and the supernatant was transferred to a new EP tube.

(6) an equal volume of phenol/chloroform/isoamyl alcohol mixture (25:24:1 by volume) were added and mixed thoroughly.

(7) the mixture was centrifuged at 13000 rpm for 5 minutes, the upper aqueous phase was carefully aspirated, the remaining was transferred to a new EP tube, 2 volumes of absolute ethanol was added, and the mixture was precipitated at −20° C. for 30 minutes.

(8) the mixture was centrifuged at 13000 rpm for 10 min, the supernatant was discarded, and the precipitate was washed once with 75% ethanol.

(9) the mixture was centrifuged at 13000 rpm for 5 min, and the supernatant was discarded.

(10) the EP tube was kept at room temperature for a few minutes, an appropriate amount of TE was added, the precipitate was resuspended, and kept at 56° C. for 30 minutes.

5. DNA product purification (refer to Tiangen manual for operation)

(1) 500 μl of balance solution BL was added to the adsorption column CB2, centrifuged at 13,000 rpm for 1 min, the waste liquid in the collection tube was discarded, and the adsorption column CB2 was put back into the collection tube.

(2) the plasmid to be purified was added, 5 times the volume of binding solution PB was added thereto, and mixed well.

(3) the solution obtained in the previous step was added to an adsorption column CB2 (the adsorption column was placed in the collection tube), placed at room temperature for 2 minutes, centrifuged at 13,000 rpm for 1 minute, the waste liquid in the collection tube was discarded, and the adsorption column CB2 was put into collection tube. Note: the volume of the adsorption column was 800 μl. If the sample volume was larger than 800 μl, it can be added in batches.

(4) 600 μl of rinsing solution PW was added to the adsorption column CB2 (please check whether absolute ethanol has been added before use), kept for 2-5 minutes and then centrifuged at 13,000 rpm for 1 minute, the waste in the collection tube Liquid was discarded, the adsorption column CB2 was put into the collection tube.

(5) step 4 was repeated.

(6) the adsorption column CB2 was put back into the collection tube, centrifuged at 13,000 rpm for 2 minutes, and the rinse liquid was removed as far as possible. The adsorption column CB2 was placed at room temperature for a few minutes, and dried thoroughly to prevent the residual rinsing solution from affecting the next experiment.

(7) the adsorption column CB2 was put into a clean centrifuge tube, and 30-50 μl elution buffer EB was dropwise added into the middle of the adsorption membrane, and the centrifuge tube was placed at room temperature for 2 minutes, and centrifuged at 13,000 rpm for 2 min to collect the DNA solution.

6. Enzyme digestion of DNA product after purification

Enzyme digestion with restriction endonuclease HindIII/XhoI was conducted at 37° C. for 1 h, followed by 1.0% agarose gel electrophoresis and observation of the enzyme digestion results, the results were shown in FIG. 5, wherein M: Marker III; lanes 1-4: HindIII/XhoI. The results showed that the strain solution contained the target fragments and the plasmid was successfully transfected into C500.

The results showed that the prepared plasmid contained tri-expression recombinant plasmids (PVAX-tPA-SAMH-2A-tPA-SINH-2A'-tPA-SRPRP-asd) of anti-müllerian hormone, inhibin and gonadotropin inhibiting hormone, it was deposited in the China Center for Type Culture Collection on Aug. 15, 2018, with a classification name: *Salmonella enterica* C500 (PVAX-SAMH-2A-SINH-2A-SRFRP-asd), and deposit number: CCTCC NO: M 2018544. PVAX-tPA-SAMH-2A-tPA-SINH-2A'-tPA-SRFRP-asd plasmid can be obtained by extraction by SDS alkaline lysis method.

Example 3: Detection of In Vitro Expression of Eukaryotic Tri-Expression Anti-müllerian Hormone, Inhibin, Gonadotropin Inhibiting Hormone Plasmid PVAX-tPA-SAMH-2A-tPA-SINH-2A'-tPA-SRFRP-asd Plasmid Detection of transcription level of PVAX-tPA-SAMH-2A-tPA-SINH-2A'-tPA-SRFRP-asd plasmid transfected cells: a plasmid extraction kit was used to extract the plasmid, when the monolayer of Hela cells (cell line of human cervical cancer cells) grew to 60%-70%, the Hela cells were transfected with Lipofectamine 3000 liposome transfection kit, followed by digestion of the cells with pancreatin and collection of cells after 48 hours. mRNA of the cells was extracted with Trizol, and cDNA was obtained by reverse transcription, which was amplified according to the primers of anti-müllerian hormone, inhibin and gonadotropin release inhibitor (see Table 3).

The cDNA obtained by reverse transcription was used as a template, the primers of AMH-INH and INH-RFRP (see Table 3) were used to amplify the two target fragments of AMH-INH and INH-RFRP. 1% agarose electrophoresis detection found 1010 bp (AMH-INH) and 1027 bp (INH-RFRP) fragments, shown in FIG. 6, wherein M: Marker III; lane 1: Primer AMH-INH negative amplification; Lane 2: Primer INH-RFRP negative amplification; Lane 3: Primer AMH-INH amplification of no treatment group; Lane 4: Primer INH-RFRP amplification of no treatment group; Lane 5: Primer AMH-INH amplification and transfection empty Group; Lane 6: Primer INH-RFRP amplification of transfection empty vector group; Lane 7: Primer AMH-INH amplification of transfection tri-expression group; Lane 8: Primer INH-RFRP amplification of transfection tri-expression group.

Example 4: Application of Eukaryotic Tri-Expression Non-Resistant DNA Plasmids of Anti-Müllerian Hormone, Inhibin, and Gonadotropin Inhibiting Hormone in Promoting the Fecundity of Animals Our laboratory used constructed non-resistant screened vaccines (PVAX-tPA-SAMH-asd, PVAX-tPA-SINH-asd, PVAX-tPA-SRFRP-asd) to immunize mice, proving that it can increase the litter size of mice. Anti-müllerian hormone, inhibin and gonadotropin inhibiting hormone gene vaccine C500 (PVAX-tPA-SAMH-asd, PVAX-tPA-SINH-asd, PVAX-tPA-SRFRP-asd with their respective non-resistance)) was used a a positive control to compare the immune effects of the new tri-gene vaccine PVAX-tPA-SAMH-2A-tPA-SINH-2A'-tPA-SRFRP-asd that was simultaneously against anti-müllerian hormone, inhibin and gonadotropin inhibiting hormone, to identify the immune effect of the vaccine, and tried to promote the application of a new type of tri-expression anti-müllerian hormone, inhibin and gonadotropin release inhibiting hormone gene vaccine in the production. The specific operations were as follows:

1 Materials and methods 1.1 Plasmids and Strains

Plasmids PVAX-tPA-SAMH-asd, PVAX-tPA-SINH-asd, PVAX-tPA-SRFRP-asd, PVAX-tPA-SAMH-2A-tPA-SRFRP-asd, PVAX-tPA-SINH-2A'-tPA-SRFRP-asd were constructed and stored by our laboratory; at the same time, *Salmonella enterica* sv. *Choleraesuis* C500 (PVAX-tPA-SAMH-2A-tPA-SINH-2A'-tPA-SRFRP-asd) simultaneously against anti-müllerian hormone, inhibin and gonadotropin release inhibiting hormone after identification was stored at −80° C.

1.2 Laboratory Animal Feeding and Management

SPF-grade 5-week-old female Kunming mice were purchased from Hubei Provincial Center for Disease Control and Prevention. After one week of pre-feeding, they were randomly divided into groups and entered the experimental period. They were raised in a special animal room in the laboratory. The feeding temperature was controlled at about 25° C. with standard feed and regular drinking water. The were raised in cages with 5 animals per cage, sanitized and cleaned once a week, and daily observed for food and water intake and health status.

1.3 Test Grouping

The Kunming female mice pre-fed for 1 week were randomly divided into the following 6 groups as shown in Table 4, 20 per group.

TABLE 4

Types and doses of immunizing vaccines in each group

| Vaccines | Immunizing dose (CFU) | Immunizing volume (μl) |
|---|---|---|
| control | PBS | 200 |
| PVAX-asd | $10^{10}$ | 200 |
| PVAX-tPA-SAMH-asd | $10^{10}$ | 200 |
| PVAX-tPA-SINH-asd | $10^{10}$ | 200 |
| PVAX-tPA-SRFRP-asd | $10^{10}$ | 200 |
| PVAX-tPA-SAMH-2A-tPA-SRFRP-asd | $10^{10}$ | 200 |
| PVAX-tPA-SINH-2A'-tPA-SRFRP-asd | $10^{10}$ | 200 |
| PVAX-tPA-SAMH-2A-tPA-SINH-2A'-tPA-SRFRP-asd | $10^{10}$ | 200 |

1.4 Immunization Methods 4 hours before immunization, the water and feed were removed from the mice, and 200 μl sodium bicarbonate (7.5%) were given by gavage first. After 30 minutes, the mice in the immunized group were given by gavage 200 μl vaccine (see Table 3 for details). Two weeks later, the same method was used to boost the immunization, and the mental and physical conditions of the mice were observed for one week after the immunization.

1.5 Weighing and Blood Collection of Mice

The mice were weighed at the same time period before immunization, 1 and 2 weeks after immunization, and body weight data were recorded. On the day of immunization and the 8th week after immunization, blood was collected from the tail vein. The blood was collected into a 1.5 ml EP tube containing 20 μl heparin sodium anticoagulant/tube, centrifuged at 3000 r/min for 10 minutes, and the upper plasma was carefully aspirated and stored at −20° C. for later use.

1.6 Statistics of Litter Size and Litter Weight after Mating of Mice

Two weeks after the boosted immunization with the vaccine, all female mice were divided into cages (2 per cage) and labeled, and healthy male mice were put into the cages until all female mice became pregnant. The litter size, litter weight and weight of newborn mouse.

1.7 Detection of AMH/INH/RFRP Antibody

The indirect ELISA method was used to detect the production of AMH, INH and RFRP antibodies in mice after immunization. The specific steps were as follows:

(1) Each well of 96-well microplate was coated with 50 ng/100 μl of AMH, INH or RFRP antigen, and incubated overnight at 4° C.

(2) The reaction solution was discarded, the plate was washed with PBST 3 times, 300 μl/well, 3 min each time.

(3) 200 μl/well of blocking solution (1% BSA solution) was added and incubated at 37° C. for 1 h.

(4) The reaction solution was discarded, the plate was washed with PBST 3 times, 300 μl/well, 3 min each time.

(5) 100 μl/well of diluted plasma to be tested was added, negative control wells, non-specific adsorption wells (PBST substituted plasma) and zero control were set, and the plated was incubate at 37° C. for 90 minutes.

(6) The reaction solution was dicarded, the plate was washed with PBST 5 times, 300 μl/well, 3 min each time.

(7) 100 μl/well of goat anti-mouse IgG-HRP (Google, 1:3000 dilution) was added, and reacted at 37° C. for 1 h.

(8) The reaction solution was discarded, and the plated was washed with PBST 5 times, 300 μl/well, 3 min each time.

(9) 150 μl/well of TMB substrate color developing solution was added and reacted for 15 min in the dark.

(10) 2 mol/L H2SO4 stop solution 50 μl/well was added to stop the reaction, and the OD value of each well was measured at 450 nm wavelength within 15 min 2 Results and Analysis 2.1 Immune Response 2.1.1 Anti-AMH Antibody Levels after Immunization of Mice with Different Vaccines The attenuated *Salmonella* C500 strain solution into which the plasmid pVAX-asd, pVAX-tPA-SAMH-asd, pVAX-tPA-SAMH-2A-tPA-SRFRP-asd or pVAX-tPA-SAMH-2A-tPA-SINH-2A'-tPA-SRFRP-asd was transformed was used to immunize mice at a dose of $10^{10}$ CFU/ml. Eight weeks after the initial immunization, blood was collected and tested for anti-AMH antibodies. It was found that the experimental groups all produced anti-AMH antibodies, and the difference between the experimental groups was not significant (P>0.05, the results were shown in FIG. 7).

2.1.2 Anti-INH Antibody Levels after Immunization of Mice with Different Vaccines The attenuated *Salmonella* C500 strain solution into which the plasmid pVAX-asd, pVAX-tPA-SINH-asd, pVAX-tPA-SINH-2A'-tPA-SRFRP-asd or pVAX-tPA-SAMH-2A-tPA-SINH-2A'-tPA-SRFRP-asd was transformed was used to immunize mice at a dose of $10^{10}$ CFU/ml. Blood was collected 8 weeks after primary immunization and tested for anti-INH antibodies. It was found that the experimental groups all produced anti-INH antibodies, and the difference between the experimental groups was not significant (P>0.05, shown in FIG. 8).

2.1.3 Anti-RFRP Antibody Levels after Immunized Mice with Different Vaccines

The attenuated *Salmonella* C500 strain solution into which the plasmid PVAX-asd, PVAX-tPA-SRFRP-asd, PVAX-tPA-SAMH-2A-tPA-SRFRP-asd, PVAX-tPA-SINH-2A'-tPA-SRFRP-asd or PVAX-tPA-SAMH-2A-tPA-SINH-2A'-tPA-SRFRP-asd was transformed was used to immunize mice at a dose of $10^{10}$ CFU/ml, and blood was collected from 8 weeks after the primary immunization and tested for anti-RFRP antibodies. It was found that the experimental group all produced Anti-RFRP antibodies, and the difference between the experimental groups was not significant (P>0.05, shown in FIG. 9).

2.2 Comparison of Litter Size and Birth Weight of Mice after Immunization with Different Vaccines Statistics of the litter size and birth weight of mice immunized with different vaccines showed that the litter size in the PVAX-tPA-SAMH-2A-tPA-SINH-2A'-tPA-SRFRP-asd group was significantly higher than that of the PBS group, pVAX-asd group, The pVAX-tPA-SAMH-asd group and pVAX-tPA-SRFRP-asd group (Table 5) and was also higher than that of the pVAX-tPA-SINH-asd group, PVAX-tPA-SAMH-2A-tPA-SRFRP-asd group and PVAX-tPA-SINH-2A'-tPA-SRFRP-asd group. Statistics of the birth weight of each group showed that genetically immunized mother mice did not affect the birth weight of newborn mice, and the difference between the groups was not significant (P>0.05).

TABLE 5

Comparison of litter size and litter weight of mice after immunization with different vaccines

| Groups | Litter size | Birth weight (g) |
|---|---|---|
| Control group | $13.6 \pm 1.72^{cC}$ | $1.76 \pm 0.09$ |
| PVAX-asd | $13.66 \pm 2.30^{cC}$ | $1.76 \pm 0.12$ |
| PVAX-tPA-SAMH-asd | $14.35 \pm 2.43^{bcBC}$ | $1.78 \pm 0.10$ |
| PVAX-tPA-SINH-asd | $14.94 \pm 2.19^{abcABC}$ | $1.76 \pm 0.12$ |
| PVAX-tPA-SRFRP-asd | $14.26 \pm 1.37^{bcBC}$ | $1.76 \pm 0.13$ |
| PVAX-tPA-SAMH-2A-tPA-SRFRP-asd | $15.50 \pm 3.14^{abABC}$ | $1.83 \pm 0.10$ |
| PVAX-tPA-SINH-2A'-tPA-SRFRP-asd | $15.44 \pm 2.13^{abABC}$ | $1.79 \pm 0.18$ |
| PVAX-tPA-SAMH-2A-tPA-SINH-2A'-tPA-SRFRP-asd | $15.93 \pm 1.90^{aAB}$ | $1.82 \pm 0.12$ |

Note:
The lowercase letters marked on the data in the same column are completely different, indicating that the difference is significant (p < 0.05), otherwise, the difference is not significant (p > 0.05), and the uppercase letters marked on the data in the same column are completely different, indicating that the difference is extremely significant (p < 0.01), and all data are expressed as mean + standard deviation.

The results indicate that the PVAX-tPA-SAMH-2A-tPA-SINH-2A'-tPA-SRFRP-asd DNA vaccine constructed by the present invention can effectively improve the fecundity of animals.

APPENDIX 1 CONSTRUCTION OF VECTOR PVAX-TPA-SINH-ASD 1.1.1 Amplification of tPA-SINH Fragment The pIRES-tPA-SINH-tPA-SRFRP plasmid was used as a template for PCR amplification. In the 20 μL PCR reaction system, the template was 1.5 μL, the upstream and downstream primers of the tPA-SINH fragment were each 1 μL, 2×Taq PCR MIX was 10 μL, ddH$_2$O was 6.5 μL. The PCR reaction program included pre-denaturating at 94° C. for 4 min, then denaturating at 94° C. for 40s, annealing at 66° C. for 30s, extending at 72° C. for 1 min, totalling 35 cycles, and finally extending at 72° C. for 10 min and 4° C. for 10 min. The upstream primer of tPA-SINH had a KpnI enzyme digestion site, and the downstream primer had an EcoRI enzyme digestion site. The primer sequence was as follows:

| Gene Name | Primer Sequence (5'-3') | Enzyme Digestion Site | Size | Annealing Temperature |
|---|---|---|---|---|
| PA-SINH | F (SEQ ID NO. 22): 5'-CC5GTACCCCGATGG ATGCAATGAAGAGA-3' | KpnI | 879 bp | 66° C. |
| | R (SEQ ID NO. 23): -5'-CGGCGGAATTCTTA AATGTATACTCTGTGG C-3' | EcoRI | | |

1.1.2 Ligation of tPA-SINH Fragment to pMD19T (Simple)

After the electrophoresis, the agarose gel of the tPA-SINH fragment was cut from the gel under ultraviolet light, and recovered according to the operating procedures of the TaKaRa MiniBEST Agarose Gel DNA Extraction Kit Ver.4.0 kit. The specific steps were as follows: 1% agarose gel electrophoresis, a single target DNA band was cut from the agarose gel under ultraviolet light and put into a clean 1.5 mL EP tube, 3 times the mass volume (100 mg=100 μL) Buffer GM was added, and mixed well to melt the gel block at room temperature, and the EP tube was flicked to make the gel melt completely. Then the melted liquid was transferred to an adsorption column, centrifuged at 12000 rpm for 1 min, the waste liquid in the collection tube was discarded, 500 μL Buffer WB was added, followed by centrifuging at 12000 rpm for 30s, washing twice; finally centrifuge at 12000 rpm for 1 min was conducted to remove trace liquid in the adsorption column. The adsorption column was transferred to a clean 1.5 mL EP tube, 30 μL Elution Buffer was added, and the tube was placed at room temperature for 2 min, and centrifuged at 12000 rpm for 1 min to elute the DNA. The purity of the recovery was detected by electrophoresis, and the concentration was measured. The collected DNA solution was used in the next experiment or stored at −20° C. for later use.

The tPA-SINH fragment was ligated to the pMD19T-simple vector. The specific steps were as follows: calculating the ligation volume ratio between the vector and the target fragment according to the recovered DNA concentration, and using SolutionI to ligate the pMD19T and tPA-SINH fragments. The ligation system was as follows:

| Components | Amount(μL) |
| --- | --- |
| pMD19T | 0.5 |
| tPA-SINH fragment | 4.5 |
| SolutionI | 5 |
| Total | 10 |

The system was mixed well, centrifuged for a short time, and ligation was conducted in a 16° C. water bath overnight.

1.1.3 Transformation of Strain (1) The competent cell DH5a was taken from −80° C. and thawed in ice bath, 10 μL of ligation product was added, mixed gently, and placed in ice bath for 30 min.

(2) The tube was placed at 42° C., followed by heat shock for 90 seconds, and then it was quickly taken out and placed in ice for 2 minutes. Do not shake the centrifuge tube during this process.

(3) 400 μL of LB liquid medium without antibiotics was added, mixed well and placed at 37° C., cultured under shaking at 200 r/min for 1h to resuscitate the strain.

(4) The tube was centrifuged at 3000 r/min for 5 min, and 4004, of supernatant was discarded.

(5) The remaining liquid was gently mixed, evenly spread on the LB solid medium containing Amp antibiotic (50 μg/mL) with a spreader, and incubated at 37° C. for 12-14h to observe whether or not transformed colonies grow.

1.1.4 Screening and Identification of Positive Clones

A single colony was taken to place in LB liquid medium containing Amp antibiotics (50 μg/mL), cultured under shaking at 37° C. at 200 r/min for about 12 hours, Tiangen kit was used for plasmid extraction, pMD19T-tPA-SINH plasmid was subjected to double enzyme digestion identification with KpnI and EcoRI. The enzyme digestion system was as follows:

| Components | Amount(μL) |
| --- | --- |
| recombinant plasmid DNA | 2 |
| KpnI | 2 |
| EcoRI | 2 |
| 10 × buffer | 2 |
| ddH$_2$O | 2 |
| Total | 10 |

The system was mixed well, centrifuged for a short time, and reacted overnight at 37° C. in a water bath.

10 μL of digested products were subjected to 1% agarose gel electrophoresis detection to screen out the suspected plasmids of pMD19T-tPA-SINH that were sent to Wuhan Tsingke Innovation Biotechnology Co., Ltd. for sequencing, and the strain solution corresponding to the correct plasmid after sequence alignment was amplified, the plasmid was extracted and stored at −20° C. for later use.

1.1.5 Enzyme Digestion and Recovery of Vector pVAX-asd and Plasmid pMD19T-tPA-SINH With reference to the Thermo manual with a small modification, the specific steps were as follows: Double enzyme digestion of pVAX-asd plasmid and pMD19T-tPA-SINH plasmid with restriction enzymes KpnI and EcoRI was performed to expose the sticky ends at both ends. The enzyme digestion system was as follows:

| Components | Amount(μL) |
| --- | --- |
| pVAX-asd or pMD19T-tPA-SINH | 5 |
| KpnI | 1 |
| EcoRI | 1 |
| 10 × Buffer | 2 |
| ddH$_2$O | 11 |
| Total | 20 |

The system was mixed well, centrifuged for a short time, and reacted overnight at 37° C. in a water bath.

After enzyme digestion, the target bands were separated by 1% agarose gel electrophoresis, and the tPA-SINH and linear pVAX-asd fragments were recovered using TaKaRa MiniBEST Agarose Gel DNA Extraction Kit Ver.4.0. After recovery, recovery purity was detected by electrophoresis and concentration was detected.

1.1.6 Ligation of the tPA-SINH Fragment to the Vector pVAX-Asd

In accordance with the operation instructions of Thermo T4 Ligase, the specific steps were as follows: Calculating the ligation ratio between the vector and the target fragment based on the detected DNA concentration after recovery, and T4 DNA Ligase was used to ligate pVAX-asd and tPA-SINH fragments. The ligation system was as follows:

| Components | Amount(μL) |
| --- | --- |
| tPA-SINH fragment | 4 |
| pVAX-asd fragment | 1 |
| T4 DNA Ligase | 1 |
| 10 × T4 DNA Ligase Buffer | 1 |
| H$_2$O | 3 |
| Total | 10 |

The system was mixed well, centrifuged for a short time, and ligated overnight at 16° C. in a water bath.

1.1.7 Preparation of χ6097 Competent Cells (Calcium Chloride Method)

A sterile inoculation loop was used to take the frozen strain χ6097 and streak it on the LB plate containing DAP (50 μg/mL), and streak it on the LB plate without DAP as a control, and the plates were incubated overnight at 37° C. The next day, a single colony that grew well was picked and cultured under shaking at 37° C. overnight in 5 mL LB liquid medium containing DAP (50 μg/mL). 1 mL of the activated culture was inoculated into 100 mL of LB liquid medium containing DAP (50 μg/mL), and cultured under shaking at 37° C. for 2.5-3 hours to make the OD600 value reach about 0.5. The strain culture was poured into a pre-cooled sterile centrifuge tube under aseptic conditions, placed in ice bath for 30 minutes, and centrifuged at 5000 r/min at 4° C. for 10 minutes, and the supernatant was discarded completely. Then the strain precipitate was gently suspended with 10 mL ice-precooled 0.1M $CaCl_2$, placed in ice bath for 30 min, and centrifuged at 4° C. 5000 r/min for 10 min, the supernatant was discarded completely, finally the precipitate was resuspended with ice-precooled 0.1M $CaCl_2$, 15% sterile glycerin with final concentration was added and mixed well. The resulting solution was divided into 100 μL/tube, which was directly used for transformation or stored in −80° C. refrigerator for later use.

1.1.8 Transformation of Strain (1) The competent cell χ6097 was taken out from −80° C. and thawed in an ice bath, 10 μL of ligation product was added, mixed gently, and placed in an ice bath for 30 min (2) The tube was placed at 42° C., followed by heat shock for 90 seconds, then the tube was quickly taken out and placed on ice for 2 minutes. Do not shake the centrifuge tube during this process.

(3) 400 μL of LB liquid medium without antibiotics was added, mixed well, and cultured under shaking at 37°, 200 r/min for 1h to resuscitate the strain.

(4) The tube was centrifuged at 3000 r/min for 5 min, and 400 μL of supernatant was discarded.

(5) The remaining liquid was gently mixed, and an LB plate without foreign substances was spread with a spreader, and incubated at 37° C. for 18-20 hours to observe whether or not transformed colonies grow.

1.1.9 Screening and Identification of Positive Clones

A single colony was placed in the LB liquid medium without any foreign substances, cultured under shaking at 37° C. 200 r/min for about 12 hours, Tiangen kit was used for plasmid extraction, and pVAX-tPA-SINH-asd plasmid was subjected to a double enzyme digestion identification with KpnI and EcoRI. The enzyme digestion system was shown as follows:

| Components | Amount(μL) |
|---|---|
| pVAX-tPA-SINH-asd | 8 |
| KpnI | 1 |
| EcoRI | 1 |
| 10 × buffer | 2 |
| ddH$_2$O | 8 |
| Total | 20 |

The system was mixed well, centrifuged for a short time, and reacted overnight at 37° C. in a water bath.

10 μL of digestion products was subjected to 1% agarose gel electrophoresis detection to screen out the suspected plasmids of pVAX-tPA-SINH-asd that was sent to Wuhan Tsingke Innovation Biotechnology Co., Ltd. for sequencing, and the train solution corresponding to the correct plasmids after sequence alignment was amplified, and the plasmid was extracted and stored at −20° C. for later use.

APPENDIX 2 CONSTRUCTION OF VECTOR PVAX-TPA-SRFRP-ASD 1.2.1 Amplification of tPA-SRFRP Fragment The specific PCR system and procedures were as shown in 1.1.2. The upstream primer of tPA-SRFRP had a KpnI enzyme digestion site, and the downstream primer had an EcoRI enzyme digestion site. The primer sequence was as follows:

| Gene name | Primer sequence (5'-3') | Enzyme digestion site | Size | Annealing temerature |
|---|---|---|---|---|
| tPA-SRFRP | F (SEQ ID NO. 24): 5'-CGGTACCCCGATGGA TGCAATGAAGAGA-3' | KpnI | 879 bp | 66°C. |
| | R (SEQ ID NO. 25): 5'-GAATTCGCGGCCGCT TAAATGTATACAAACC-3 | EcoRI | | |

1.2.2 Ligation of tPA-SINH Fragment and pMD19T (Simple)

Refer to 1.1.2. for specific steps.

1.2.3 Transformation of Strain

Refer to 1.1.3 for specific steps.

1.2.4 Screening and Identification of Positive Clones

Refer to 1.1.4 for specific steps.

1.2.5 Enzyme Digestion and Recovery of Vector pVAX-Asd and Plasmid pMD19T-tPA-SINH Refer to 1.1.5 for specific steps.

1.2.6 Target Gene Ligation

In accordance with the operation instructions of Thermo T4 Ligase. The specific steps were as follows: Calculating the ligation ratio between the vector and the target fragment according to the DNA concentration detected after recovery, and T4 DNA Ligase was used to ligate pVAX-asd and tPA-SRFRP fragments. The ligation system was shown as follows:

| Components | Amount(μL) |
|---|---|
| tPA-SRFRP fragment | 4.5 |
| pVAX-asd fragment | 0.5 |
| T4 DNA Ligase | 1 |
| 10 × T4 DNA Ligase Buffer | 1 |
| H$_2$O | 3 |
| Total | 10 |

The system was mixed well, centrifuged for a short time, and ligated overnight at 16° C. in a water bath.

1.2.7 Transformation of Strain

Refer to 1.1.8 for the specific process.

1.2.8 Screening and Identification of Positive Clones

Refer to 1.1.9 for the specific process.

APPENDIX 3 CONSTRUCTION OF VECTOR PVAX-TPA-SAMH-ASD

1.3.1 Synthesis of tPA-SAMH Fragment

The corresponding base sequence of the screened AMH epitope antigen-encoding gene was found out from NCBI, which was inserted into the 5' end of the hepatitis B surface antigen, the tPA signal peptide was inserted at the 3' end of the hepatitis B surface antigen, and two enzyme digestion sites, BamH I and EcoR I, were added in the upstream and downstream to form a tPA-SAMH fragment, which was sent to Sangon Biotech for synthesis.

1.3.2 Enzyme Digestion and Recovery of Vector pVAX-Asd and Plasmid pUC-tPA-SAMH
Refer to 1.1.5 for the specific process.

1.3.3 Target Gene Ligation
Refer to 1.1.2. for specific steps.

1.3.4 Strain Transformation
Refer to 1.1.8 for specific steps.

1.3.5 Screening and Identification of Positive Clones
Refer to 1.1.9 for the specific process.

What is claimed is:

1. An Anti-Müllerian hormone (AMH)-Inhibin (INH)-Gonadotropin release inhibiting hormone (GNIH) (AMH-INH-GNIH) tri-expression gene vaccine for improving the fecundity of animals, including a Tissue-type plasminogen activator- (TPA)-Hepatitis B surface antigen S gene (S)-Anti-Müllerian hormone (AMH)(tPA-SAMH) gene, a Tissue-type plasminogen activator-(TPA)-Hepatitis B surface antigen S gene (S)-Inhibin (INH) (tPA-SINH gene) and a Tissue-type plasminogen activator-(TPA)-Hepatitis B surface antigen S gene (S)-Gonadotropin release inhibiting hormone (GNIH) (tPA-SRFRP) gene in sequence.

2. The tri-expression gene vaccine according to claim 1, wherein the gene sequence of tPA-SINH is shown in SEQ ID NO. 1, the gene sequence of tPA-SRFRP is shown in SEQ ID NO. 2 and the gene sequence of the tPA-SAMH is shown in SEQ ID NO.3.

3. The tri-expression gene vaccine according to claim 1, wherein a 2A peptide is ligated between the tPA-SAMH gene and the tPA-SINH gene, a 2A' peptide is ligated between the tPA-SINH gene and the tPA-SRFRP gene, the gene sequence of the 2A peptide is shown in SEQ ID NO.4; and the gene sequence of the 2A' peptide is shown in SEQ ID NO.5.

4. An engineering strain containing the AMH-INH-GNIH tri-expression gene vaccine according to claim 1.

5. The engineering strain according to claim 4, wherein the engineering strain is deposited at the China Center for Type Culture Collection on Aug. 15, 2018, with a deposit number: CCTCC NO: M 2018544.

6. A method for preparation of an Anti-Müllerian hormone (AMH)- Inhibin (INH)-Gonadotropin release inhibiting hormone (GNIH) (AMH-INH-GNIH) tri- expression gene vaccine for improving the fecundity of animals, including the following steps:

S1. Construction of dual expression plasmids PVAX-Tissue-type plasminogen activator-(TPA)- Hepatitis B surface antigen S gene (S)- Anti-Müllerian hormone (AMH)-2A peptides-Tissue- type plasminogen activator-(TPA)-Hepatitis B surface antigen S gene (S)-RFamide-related peptide (RFRP)-aspartate-semialdehyde dehydrogenase (asd) (PVAX-tPA-SAMH-2A-tPA-SRFRP-asd) and PVAX-Tissue-type plasminogen activator- (TPA)-Hepatitis B surface antigen S gene (S)-Inhibin (INH)-2A peptides-Tissue- type plasminogen activator-(TPA)-Hepatitis B surface antigen S gene (S)-RFamide-related peptide (RFRP)-aspartate-semialdehyde dehydrogenase (asd) (PVAX-tPA-SINH-2A'-tPA- SRFRP-asd);

S2. Enzyme digestion of the plasmids obtained in step S1 with Hind III and BamHI, respectively, followed by ligation to obtain a tri-expression plasmid PVAX-Tissue- type plasminogen activator-(TPA)-Hepatitis B surface antigen S gene (S)-Anti-Müllerian hormone (AMH)-2A peptides-Tissue-type plasminogen activator-(TPA)-Hepatitis B surface antigen S gene (S)-Inhibin (INH)-aspartate-semialdehyde dehydrogenase (asd) (PVAX-tPA-SAMH-2A-tPA-SINH-2A'-tPA-SRFRP-asd).

7. The method according to claim 6, wherein the plasmid PVAX-tPA-SINH-2A'-tPA-SRFRP-asd is constructed according to the following method:

S1101, Using PVAX-tPA-SINH-asd as a template to amplify the tPA-SINH gene fragment; in which the gene sequence of the tPA-SINH PCR is shown in SEQ ID NO.1, Using PVAX-tPA-SRFRP-asd as a template to amplify the tPA-SRFRP gene fragment; in which the gene sequence of the tPA-SRFRP gene fragment is shown in SEQ ID NO.2.

S1102 Enzyme digesting the PCR products of pVAX-asd and tPA-SRFRF with EcoRI and XhoI, followed by ligation to obtain a plasmid PVAX-tPA-SRFRP-asd;

S1103. Enzyme digesting the PCR products of PVAX-tPA-SRFRP-asd and tPA-SINH with BamH I and EcoRI, followed by ligation to obtain a plasmid PVAX-tPA-SINH-tPA-SRFRP-asd;

S1104. Enzyme digesting the plasmids PVAX-tPA-SINH-tPA-SRFRP-asd and PUC57-2A'-2A with EcoRI, followed by ligation to obtain a plasmid PVAX-tPA-SINH-2A'-tPA-SRFRP-asd; wherein the gene sequence of the 2A' peptide is shown in SEQ ID NO.5.

8. The method according to claim 6, wherein the plasmid PVAX-tPA-SAMH-2A-tPA-SRFRP-asd is constructed according to the following method:

S1201. Enzyme digesting the PCR products of PVAX-tPA-SRFRP-asd and tPA-SAMH with Hind III and Kpn I, followed by ligation to obtain a plasmid PVAX-tPA-SAMH-tPA-SRFRP-asd; the gene sequence of the tPA-SAMH PCR product is shown in SEQ ID NO.3;

S1202. Enzyme digesting the plasmids PVAX-tPA-SAMH-tPA-SRFRP-asd and PUC57-2A'-2A with Kpn I and BamH I, followed by ligation to obtain a plasmid PVAX-tPA-SAMH-2A-tPA-SRFRP-asd; the gene sequence of the 2A peptide is shown in SEQ ID NO.4;

S1203. Enzyme digesting the plasmids PVAX-tPA-SAMH-2A-tPA-SRFRP-asd and PVAX-tPA-SINH-2A'-tPA-SRFRP-asd with Hind III and BamH I, followed by ligation to obtain a plasmid PVAX-tPA-SAMH-2A-tPA-SINH-2A'-tPA-SRFRP-asd.

* * * * *

SEQUENCE LISTING

<160> NUMBER OF SEQ ID NOS: 25

<210> SEQ ID NO 1
<211> LENGTH: 867
<212> TYPE: DNA
<213> ORGANISM: Artificial Sequence
<220> FEATURE:
<223> OTHER INFORMATION: gene sequence of tPA-SINH

<400> SEQUENCE: 1

```
ggatccgcca ccatggatgc aatgaagaga gggctctgct gtgtgctgct gctgtgtgga      60
gcagtcttcg tttcgcccag cgctagcatg gagagcacaa catcaggatt cctaggaccc     120
ctgctcgtgt tacaggcggg gttttcttg ttgacaagaa tcctcacaat accacagagt      180
ctagactcgt ggtggacttc tctcaatttt ctaggggag cacccacgtg tcctggccaa      240
aattcgcagt ccccaacctc caatcactca ccaacctctt gtcctccaat ttgtcctggc     300
tatcgctgga tgtgtctgcg gcgttttatc atattcctct tcatcctgct gctatgcctc     360
atcttcttgt tggttcttct ggactaccaa ggtatgttgc ccgtttgtcc tctacttcca     420
ggaacatcaa ctaccagcac gggaccatgc aagacctgca cgattcctgc tcaaggaacc     480
tctatgtttc cctcttgctg ctgtacaaaa ccttcggacg gaaactgcac ttgtattccc     540
atcccatcat cctgggcttt cgcaagattc ctatgggagt gggcctcagt ccgtttctcc     600
tggctcagtt tactagtgcc atttgttcag tggttcgtag ggctttcccc cactgtttgg     660
ctttcagtta tatggatgat gtggtattgg gggccaagtc tgtacaacat cttgagtccc     720
tttttacctc tattaccaat tttcttttgt ctttggcata tgtccaccgc ccctctgccc     780
tggccttggt ccccgccgc gctgcgcctg ctgcagaggc ccccggagga acccgctgtg      840
cacgccgact gccacagaca agaattc                                          867
```

<210> SEQ ID NO 2
<211> LENGTH: 864
<212> TYPE: DNA
<213> ORGANISM: Artificial Sequence
<220> FEATURE:
<223> OTHER INFORMATION: gene sequence of tPA-SRFRP

<400> SEQUENCE: 2

```
gaattcgcca ccatggatgc aatgaagaga gggctctgct gtgtgctgct gctgtgtgga      60
gcagtcttcg tttcgcccag cgtcgacatg gagagcacaa catcaggatt cctaggaccc     120
ctgctcgtgt tacaggcggg gttttcttg ttgacaagaa tcctcacaat accacagagt      180
ctagactcgt ggtggacttc tctcaatttt ctaggggag cacccacgtg tcctggccaa      240
aattcgcagt ccccaacctc caatcactca ccaacctctt gtcctccaat ttgtcctggc     300
tatcgctgga tgtgtctgcg gcgttttatc atattcctct tcatcctgct gctatgcctc     360
```

| | |
|---|---|
| atcttcttgt tggttcttct ggactaccaa ggtatgttgc ccgtttgtcc tctacttcca | 420 |
| ggaacatcaa ctaccagcac gggaccatgc aagacctgca cgattcctgc tcaaggaacc | 480 |
| tctatgtttc cctcttgctg ctgtacaaaa ccttcggacg gaaactgcac ttgtattccc | 540 |
| atcccatcat cctgggcttt cgcaagattc ctatgggagt gggcctcagt ccgtttctcc | 600 |
| tggctcagtt tactagtgcc atttgttcag tggttcgtag ggctttcccc cactgtttgg | 660 |
| ctttcagtta tatggatgat gtggtattgg gggccaagtc tgtacaacat cttgagtccc | 720 |
| ttttaccctc tattaccaat tttcttttgt ctttggcata tggcgatggc ccacctgcct | 780 |
| ctgagactcg gaaaaaatag agaggacagc ctctccagat gggtcccaaa tctgccccag | 840 |
| aggtttgtat acatttaact cgag | 864 |

<210> SEQ ID NO 3
<211> LENGTH: 837
<212> TYPE: DNA
<213> ORGANISM: Artificial Sequence
<220> FEATURE:
<223> OTHER INFORMATION: gene sequence of tPA-SAMH

<400> SEQUENCE: 3

| | |
|---|---|
| aagcttgcca ccatggatgc aatgaagaga gggctctgct gtgtgctgct gctgtgtgga | 60 |
| gcagtcttcg tttcgcccag catggagagc acaacatcag gattcctagg accCctgctc | 120 |
| gtgttacagg cggggttttt cttgttgaca agaatcctca caataccaca gagtctagac | 180 |
| tcgtggtgga cttctctcaa ttttctaggg ggagcaccca cgtgtcctgg ccaaaattcg | 240 |
| cagtccccaa cctccaatca ctcaccaacc tcttgtcctc caatttgtcc tggctatcgc | 300 |
| tggatgtgtc tgcggcgttt tatcatattc ctcttcatcc tgctgctatg cctcatcttc | 360 |
| ttgttggttc ttctggacta ccaaggtatg ttgcccgttt gtcctctact tccaggaaca | 420 |
| tcaactacca gcacgggacc atgcaagacc tgcacgattc ctgctcaagg aacctctatg | 480 |
| tttccctctt gctgctgtac aaaaccttcg gacggaaact gcacttgtat tcccatccca | 540 |
| tcatcctggg ctttcgcaag attcctatgg gagtgggcct cagtccgttt ctcctggctc | 600 |
| agttactag tgccatttgt tcagtggttc gtagggcttt ccccccactgt ttggctttca | 660 |
| gttatatgga tgatgtggta ttgggggcca agtctgtaca acatcttgag tccttttta | 720 |
| cctctattac caattttctt ttgtctttgg catatgaggg aagaggtctc aatacctca | 780 |
| gcctcgccca gggagcaggc acaggcagc gggacactca tctttcagca aggtacc | 837 |

<210> SEQ ID NO 4
<211> LENGTH: 75
<212> TYPE: DNA
<213> ORGANISM: Artificial Sequence
<220> FEATURE:
<223> OTHER INFORMATION: gene sequence of the 2A peptide

<400> SEQUENCE: 4

| | |
|---|---|
| ggtaccggca gtggagaggg cagaggaagt ctgctaacat gcggtgacgt cgaggagaat | 60 |
| cctggcccag gatcc | 75 |

<210> SEQ ID NO 5
<211> LENGTH: 75
<212> TYPE: DNA
<213> ORGANISM: Artificial Sequence
<220> FEATURE:
<223> OTHER INFORMATION: gene sequence of the 2A' peptide

<400> SEQUENCE: 5

```
gaattcggca gtggagaggg cagaggaagt ctgctaacat gcggtgacgt cgaggagaat    60
cctggcccag aattc                                                    75
```

<210> SEQ ID NO 6
<211> LENGTH: 37
<212> TYPE: DNA
<213> ORGANISM: Artificial Sequence
<220> FEATURE:
<223> OTHER INFORMATION: Primer Sequence

<400> SEQUENCE: 6

```
cgcggatccg ccaccatgga tgcaatgaag agagggc                            37
```

<210> SEQ ID NO 7
<211> LENGTH: 28
<212> TYPE: DNA
<213> ORGANISM: Artificial Sequence
<220> FEATURE:
<223> OTHER INFORMATION: Primer Sequence

<400> SEQUENCE: 7

```
ccggaattct tgtctgtggc agtcggcg                                      28
```

<210> SEQ ID NO 8
<211> LENGTH: 37
<212> TYPE: DNA
<213> ORGANISM: Artificial Sequence
<220> FEATURE:
<223> OTHER INFORMATION: Primer Sequence

<400> SEQUENCE: 8

```
ccggaattcg ccaccatgga tgcaatgaag agagggc                            37
```

<210> SEQ ID NO 9
<211> LENGTH: 34
<212> TYPE: DNA
<213> ORGANISM: Artificial Sequence
<220> FEATURE:
<223> OTHER INFORMATION: Primer Sequence

<400> SEQUENCE: 9

```
ccgctcgagt taaatgtata caaacctctg gggc                               34
```

<210> SEQ ID NO 10
<211> LENGTH: 37
<212> TYPE: DNA
<213> ORGANISM: Artificial Sequence
<220> FEATURE:
<223> OTHER INFORMATION: Primer Sequence

<400> SEQUENCE: 10

```
ccgaagcttg ccaccatgga tgcaatgaag agagggc                            37
```

<210> SEQ ID NO 11
<211> LENGTH: 31
<212> TYPE: DNA
<213> ORGANISM: Artificial Sequence
<220> FEATURE:
<223> OTHER INFORMATION: Primer Sequence

<400> SEQUENCE: 11

```
ccgggtacct tgctgaaaga tgagtgtccc g                                  31
```

<210> SEQ ID NO 12

```
<211> LENGTH: 23
<212> TYPE: DNA
<213> ORGANISM: Artificial Sequence
<220> FEATURE:
<223> OTHER INFORMATION: Primer Sequence

<400> SEQUENCE: 12
tacgcgcata caacaaaagt cgc                                              23

<210> SEQ ID NO 13
<211> LENGTH: 23
<212> TYPE: DNA
<213> ORGANISM: Artificial Sequence
<220> FEATURE:
<223> OTHER INFORMATION: Primer Sequence

<400> SEQUENCE: 13
gccattctga cggaattaac ggg                                              23

<210> SEQ ID NO 14
<211> LENGTH: 20
<212> TYPE: DNA
<213> ORGANISM: Artificial Sequence
<220> FEATURE:
<223> OTHER INFORMATION: Primer Sequence

<400> SEQUENCE: 14
ttgctttcca actgctgagc                                                  20

<210> SEQ ID NO 15
<211> LENGTH: 20
<212> TYPE: DNA
<213> ORGANISM: Artificial Sequence
<220> FEATURE:
<223> OTHER INFORMATION: Primer Sequence

<400> SEQUENCE: 15
tcctatctgc gtcgtcctac                                                  20

<210> SEQ ID NO 16
<211> LENGTH: 20
<212> TYPE: DNA
<213> ORGANISM: Artificial Sequence
<220> FEATURE:
<223> OTHER INFORMATION: Primer Sequence

<400> SEQUENCE: 16
caggatacct atagtgctgc                                                  20

<210> SEQ ID NO 17
<211> LENGTH: 20
<212> TYPE: DNA
<213> ORGANISM: Artificial Sequence
<220> FEATURE:
<223> OTHER INFORMATION: Primer Sequence

<400> SEQUENCE: 17
cgcaccgtca aaggaaccgt                                                  20

<210> SEQ ID NO 18
<211> LENGTH: 19
<212> TYPE: DNA
<213> ORGANISM: Artificial Sequence
<220> FEATURE:
<223> OTHER INFORMATION: Primer Sequence

<400> SEQUENCE: 18
```

-continued tatgtccacc gcccctctg                    19

<210> SEQ ID NO 19
<211> LENGTH: 23
<212> TYPE: DNA
<213> ORGANISM: Artificial Sequence
<220> FEATURE:
<223> OTHER INFORMATION: Primer Sequence

<400> SEQUENCE: 19
aatgtataca aacctctggg gca               23

<210> SEQ ID NO 20
<211> LENGTH: 22
<212> TYPE: DNA
<213> ORGANISM: Artificial Sequence
<220> FEATURE:
<223> OTHER INFORMATION: Primer Sequence

<400> SEQUENCE: 20
atgagggaag aggtctccaa ta                22

<210> SEQ ID NO 21
<211> LENGTH: 20
<212> TYPE: DNA
<213> ORGANISM: Artificial Sequence
<220> FEATURE:
<223> OTHER INFORMATION: Primer Sequence

<400> SEQUENCE: 21
tcttgtctgt ggcagtcggc                   20

<210> SEQ ID NO 22
<211> LENGTH: 28
<212> TYPE: DNA
<213> ORGANISM: Artificial Sequence
<220> FEATURE:
<223> OTHER INFORMATION: Primer Sequence

<400> SEQUENCE: 22
cggtaccccg atggatgcaa tgaagaga         28

<210> SEQ ID NO 23
<211> LENGTH: 31
<212> TYPE: DNA
<213> ORGANISM: Artificial Sequence
<220> FEATURE:
<223> OTHER INFORMATION: Primer Sequence

<400> SEQUENCE: 23
cggcggaatt cttaaatgta tactctgtgg c      31

<210> SEQ ID NO 24
<211> LENGTH: 28
<212> TYPE: DNA
<213> ORGANISM: Artificial Sequence
<220> FEATURE:
<223> OTHER INFORMATION: Primer Sequence

<400> SEQUENCE: 24
cggtaccccg atggatgcaa tgaagaga         28

<210> SEQ ID NO 25
<211> LENGTH: 31
<212> TYPE: DNA

```
<213> ORGANISM: Artificial Sequence
<220> FEATURE:
<223> OTHER INFORMATION: Primer Sequence

<400> SEQUENCE: 25
gaattcgcgg ccgcttaaat gtatacaaac c                                    31
```